United States Patent [19]
Phelps et al.

[11] Patent Number: 5,339,766
[45] Date of Patent: Aug. 23, 1994

[54] METHOD OF INTRODUCING MATERIAL INTO EGGS DURING EARLY EMBRYONIC DEVELOPMENT

[75] Inventors: Patricia V. Phelps, Raleigh; Julius K. Tyczkowski, Cary; Toni O. O'Connell, Zebulon; Ann B. Gore, Raleigh, all of N.C.

[73] Assignee: Embrex, Inc., Research Triangle Park, N.C.

[21] Appl. No.: 147,162

[22] Filed: Nov. 3, 1993

[51] Int. Cl.[5] ............................................. A01K 67/00
[52] U.S. Cl. ................................................... 119/6.8
[58] Field of Search ........................... 119/6.8, 6.6, 174

[56] References Cited

U.S. PATENT DOCUMENTS

| | | |
|---|---|---|
| 2,477,752 | 8/1949 | Kiss . |
| 2,734,482 | 2/1956 | Seltzer . |
| 3,256,856 | 6/1966 | Nicely et al. . |
| 3,377,989 | 4/1968 | Sandhage et al. . |
| 4,040,388 | 8/1977 | Miller . |
| 4,469,047 | 9/1984 | Miller .................................. 119/6.8 |
| 4,593,646 | 6/1986 | Miller et al. . |
| 4,681,063 | 7/1987 | Hebrank . |
| 4,903,635 | 2/1990 | Hebrank . |
| 4,928,628 | 5/1990 | Gassman et al. . |
| 4,928,629 | 5/1990 | Trampel . |
| 5,056,464 | 10/1991 | Lewis . |
| 5,136,979 | 8/1992 | Paul et al. . |
| 5,176,101 | 6/1993 | Paul et al. . |
| 5,206,015 | 5/1993 | Cox et al. ............................. 119/6.8 |

*Primary Examiner*—John G. Weiss
*Attorney, Agent, or Firm*—Bell, Seltzer, Park & Gibson

[57] ABSTRACT

A method of introducing a substance into a bird egg through the shell thereof comprises the steps of applying a seal to the exterior of the shell, inserting an injection device through the seal and into the egg, injecting the substance through the injection device and into the interior of the egg, and withdrawing the injection device from the egg through the seal. The method is particularly preferred for injecting substances into the albumin during the first quarter of injection through the bottom of the egg when the small end of the egg is oriented downward to prevent the introduction of air bubbles through the opening formed in the shell by the injection device.

22 Claims, 1 Drawing Sheet

FIG. 1
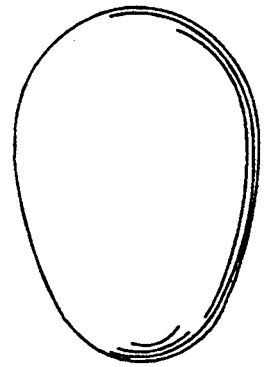
FIG. 3
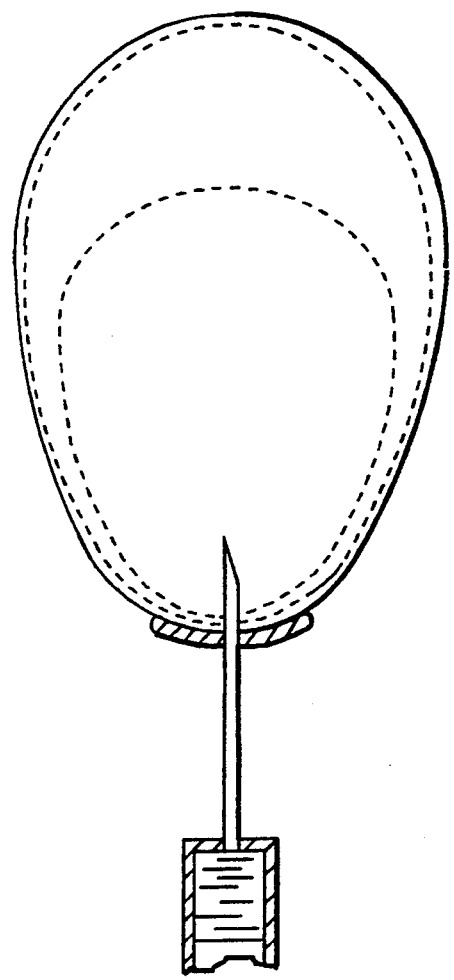
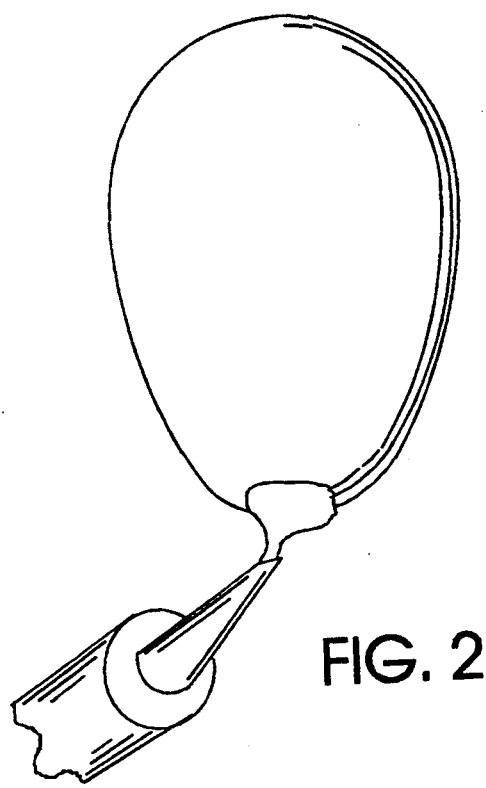
FIG. 2

METHOD OF INTRODUCING MATERIAL INTO EGGS DURING EARLY EMBRYONIC DEVELOPMENT

FIELD OF THE INVENTION

The present invention relates to a method of introducing material into eggs during early embryonic development.

BACKGROUND OF THE INVENTION

The desirability of injecting materials into avian eggs during incubation has been recognized for some time. Initially, the purpose of injecting eggs was to prepare various vaccines using the egg as a growth medium for the vaccine. More recent developments have involved injecting live embryonated eggs for the purpose of accomplishing some beneficial or therapeutic effect on the embryo or the bird that eventually hatches from the egg. Such beneficial effects include increased growth, disease resistance due to in ovo vaccination, increased percentage hatch of multiple incubated eggs, and otherwise improved physical characteristics of hatched poultry.

Several basic techniques and injection devices for injecting materials into live embryonated eggs have been described, including forcing fluids through the egg shell using pressurization and physically forming an opening in the shell of an egg and then adding the desired material (e.g., injection using syringe and needle arrangements). One traditional method has been syringe injection of eggs by hand.

Several injection devices seal the injection hole after injection to prevent leakage and contamination. U.S. Pat. No. 4,593,646 to Miller et al. discloses a method and apparatus for automatic egg injection in which support plates hold and properly position a plurality of injection devices and eggs. Each egg is sealed after injection by heat coagulating the albumin located near the injection hole. An additional sealant is then applied to the outer shell by dipping each egg into a bath of the sealant. The '646 patent does not disclose sealing the egg prior to injection.

U.S. Pat. No. 4,040,388 to Miller discloses a method and apparatus for automatic egg injection in which the downwardly facing small end of an egg is punctured. The portion of the device which punctures the egg is heated in the '388 method, allegedly sterilizing the exterior of the egg (thus preventing infection during injection) and also sealing the hole by heat coagulating a small portion of the egg albumin. The '388 patent does not disclose sealing the egg prior to injection.

U.S. Pat. No. 2,477,752 to Kiss discloses a method of injecting fertile eggs for the purpose of producing chicks having down of predetermined colors. The '752 patent discloses injecting the egg manually with a syringe and thereafter by sealing the opening in the egg. While the patent states that care should be taken to prevent air from entering the egg, no method for preventing the entrance of air is provided. Sealing the egg prior to injection is not disclosed.

U.S. Pat. No. 5,136,979 to Paul et al. discloses an apparatus and method for injecting a plurality of eggs to the same depth and location even when the eggs are of varying sizes and are misaligned. The apparatus includes a means for sterilizing the egg punch and needle sections after each injection. U.S. Pat. No. 5,056,464 to Lewis discloses an apparatus and method for injecting a plurality of eggs in which a suction cup apparatus is used for grasping each egg. U.S. Pat. No. 4,903,635 to Hebrank discloses a high speed automated injection system in which eggs are lifted using suction devices and separate devices are used for forming an opening in the egg shell and for injecting a fluid substance.

Some egg injection devices deliver material through the small end of an egg into the albumin. Injecting material through the large end of an egg and into the air sac above the albumin is not appropriate for delivery of all materials. Delivery into the albumin, however, increases the risk of leakage of albumin and ingress of air and contaminants after injection. Methods of injecting material into the albumin of eggs on a rapid basis should preferably provide means for preventing air and contaminants from entering the albumin, and means for preventing leakage of albumin, after injection.

SUMMARY OF THE INVENTION

A first aspect of the present invention is a method of injecting a desired substance into an avian egg through the egg shell, comprising applying sealant to the exterior of the shell at the injection site, inserting an injection device through the sealant and into the egg (preferably the albumin of the egg), injecting a preselected substance into the egg (preferably the albumin of the egg), and withdrawing the injection device from the egg. The sealant serves to seal the opening which would otherwise remain upon withdrawal of the injection device. The egg may then be incubated to hatch.

In one embodiment of the present invention, the applying step comprises the steps of, first, depositing a liquid sealant material on the egg, and then curing the liquid sealant on the egg to form an elastic seal thereon. In another embodiment of the invention, the applying step comprises the steps of, first, providing a preformed elastic seal member, and then adhering the preformed elastic seal member to the egg.

The foregoing and other objects and aspects of the present invention are explained in detail in the drawings herein and the specification set forth below.

DETAILED DESCRIPTION OF THE INVENTION

The present invention includes a method for injecting eggs to minimize the ingress of air and contaminants, and minimize the leakage of albumin from the egg.

To inject eggs using the method of the present invention, a sealant is first applied at the site of injection. While injection may occur at any site whereby the material injected is placed in the albumin, a particularly preferred site is the small end (bottom) of the egg. Sealant may be any suitable resilient or elastic material which allows the needle to be inserted through the sealant while essentially preventing the entry of air through the injection site into the egg during injection and subsequent incubation. Examples of suitable sealants include silicone sealants (e.g., G.E. TM Silicone II), adhesives or glues (e.g., DUCO TM cement, mucilage glue), hot melt adhesives, or any other liquid which solidifies and hardens after application and through which a needle can be inserted, yet which retains sufficient elasticity that a syringe or needle can be inserted and withdrawn therethrough with subsequent sealing of the hole made thereby. Alternatively, a glue or adhesive may be used to attach another component to the egg through which the injection occurs, and which acts to prevent air entry into the egg (e.g., a rubber or silicone septum attached firmly to the egg surface).

Figure 1:
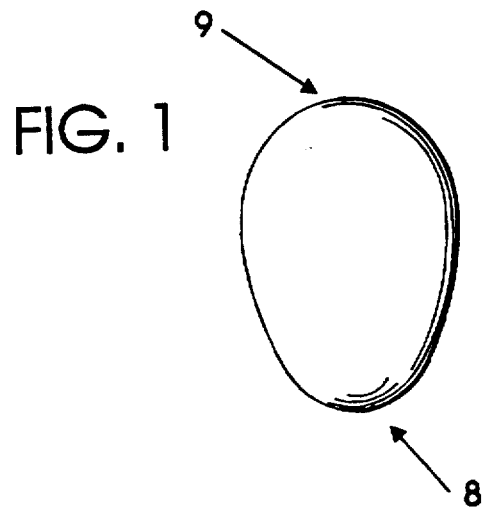
FIG. 1 is a schematic view of an arian egg showing the proper orientation of an egg during incubation, with the large end of the egg pointing upwards, as such an egg may be oriented for carrying out the present invention.
Figure 2:
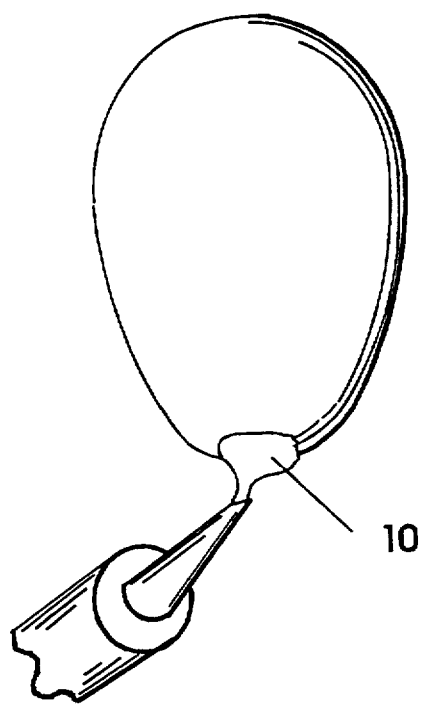
FIG. 2 shows the deposition of sealant on an egg prior to insertion of an injection device in accordance with the present invention.
Figure 3:
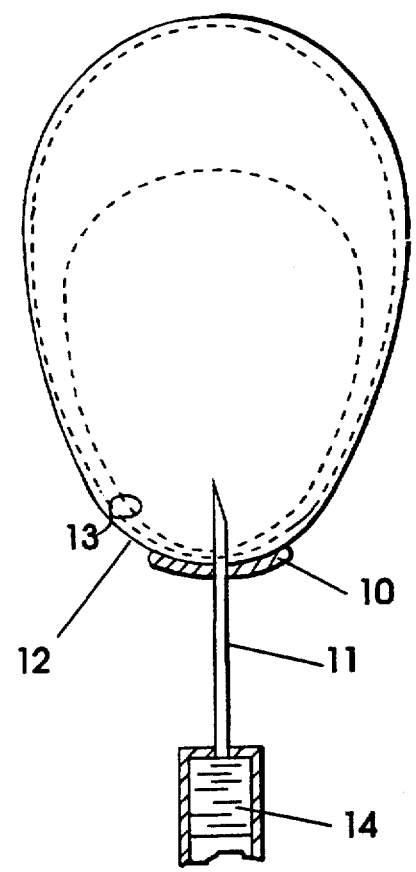
FIG. 3 shows an egg with an injection device inserted through the sealant and into the albumin of the egg in accordance with the present invention.

FIG. 1 is a schematic depiction of an egg with the small end (bottom) 8 oriented downward and the large end (top) 9 oriented upward. As shown in FIG. 2, in practicing the present invention, sealant (10) is applied to the egg shell at the site of injection. As shown in FIG. 3, after the sealant (10) is applied to the egg surface, an injection needle (11) or other injection device is inserted through the sealant and underlying egg shell (12) and membranes (13), and the material to be injected (14) is expelled in the interior of the egg. In general, a portion of the shell is left unsealed, which unsealed portion is sufficient in size to permit respiration of the embryo within the egg during incubation so that the embryo may be incubated to hatch. Preferably a major portion of the egg shell remains unsealed, with the sealed portion preferably including the small end (bottom) of the egg.

The materials or substances to be delivered include, but are not limited to vaccines, vitamins, antibiotics, hormones, enzyme inhibitors, peptides, cells, DNA, and other therapeutic molecules. Materials or substances may be fluids, liquids, solutions, liquid-liquid suspensions, liquid-solid suspensions, gases, gaseous suspensions, emulsions, and solid materials such as biodegradable polymers (e.g., in the form of syringeable beads) which release active agents such as described above upon biodegredation. Examples of biodegradable polymers include, but are not limited to, polylactide polymers, including lactide/glycolide copolymers. See, e.g., U.S. Pat. Nos. 3,773,919, 4,568,559, and 4,389,330 (the disclosures of which applicant specifically intend to be incorporated herein by reference).

The surface of the egg may optionally be sanitized prior to injection by any suitable method. Examples of suitable sanitizing compounds include formaldehyde, $H_2O_2$ (e.g., 3% $H_2O_2$, 5% $H_2O_2$, 5% $H_2O_2$ combined with a quaternary ammonium agent), chlorine based sanitizers, or other commercially available egg sanitizers. Any suitable method of applying a sanitizing compound may be used, including but not limited to fumigation, microaerosol fumigation, dipping of whole egg, direct application to egg, vacuum application to egg, or other techniques as are known in the art.

The seal may carry or contain an antibacterial agent such as GARISOL TM, so that when the needle or injection device is inserted through the seal it is sanitized by contact to the antibacterial agent contained in or carried by the seal.

The term "birds" as used herein, is intended to include males or females of any avian species, but is primarily intended to encompass poultry which are commercially raised for eggs or meat. Accordingly, the term "bird" is particularly intended to encompass hens, cocks and drakes of chickens, turkeys, ducks, geese, quail, ostriches and pheasants. Chickens and turkeys are preferred.

The term "in ovo," as used herein, refers to birds contained within an egg prior to hatch. Thus, the present invention may be conceived of as both a method of introducing a compound into an egg as well as a method of administering a substance to a bird. The present invention may be practiced with any type of bird egg, including chicken, turkey, duck, goose, quail, ostrich and pheasant eggs. Chicken and turkey eggs are preferred. Any region within the egg may be injected, including the region defined by the amnion (including the embryo), the albumin, and the yolk sac (preferably the albumin). Eggs treated by the method of the present invention are preferably fertile eggs which may be in any period of incubation, from early to late, but are preferably in the first half of incubation. More preferably, eggs are in the first quarter of incubation. Selection of the time of injection will depend upon the agent being injected and the desired effect, and will be ascertainable by one skilled in the art.

The term "Day 0" as used herein refers to eggs prior to incubation.

The present invention is particularly advantageous for injecting the albumin of eggs during early embryonic development without significantly decreasing hatchability. When injecting early embryonic eggs in the albumin, introduction of an air bubble can interfere with the development of the embryo and result in decreased hatchability rates. The method of the present invention allows injection into the albumin at Day 0 of incubation with good hatchability rates. The use of a sealant prior to injection essentially prevents the introduction of air into the egg and reduces bacterial contamination caused by the introduction of a needle and exposure of internal egg contents to the external environment.

The following examples are provided to illustrate the present invention, and should not be construed as limiting thereof. In these examples, $\mu l$ means microliter, ml means milliliter, mg means milligram, and (CFU means colony forming units).

EXAMPLE 1

Decreased Hatchability Due to Air Bubble

In initial attempts to inject Day 0 eggs, the eggs were injected through the small end while held upside down (small end up); this resulted in hatchability rates of from 5-8%, regardless of the sanitation measures used on the eggs prior to injection (data not shown). Using illumination and visual examination of injected eggs, it was noted that eggs injected in this manner were developing abnormally, for example, eggs were noted to have frothy albumin, absent aircells, or aircells that moved as the egg was rotated. Illumination and examination of eggs during injection revealed that an air bubble entered the egg through the injection site. If the egg was inverted during injection and then turned right-side up for incubation, the bubble rose and rested between the inner shell membrane and the developing blastodisc (early embryo). When the egg was injected through the small end while held upright, either no air bubble entered the egg or it did not rise to the top of the egg. Hatchability data of noninjected control eggs, eggs injected (small end) while inverted, and eggs injected (small end) while held upright are shown in Table 1.

TABLE 1

Hatchability Following Injection[1].

| TREATMENT | AIR BUBBLE INTERFERENCE | HATCHABILITY | EGGS OBSERVED (n) |
|---|---|---|---|
| NONINJECTED CONTROLS | NO | 83% | 100 |
| BOTTOM (small end) INJECTED; EGGS INVERTED | YES | 4% | 100 |
| BOTTOM (small end) INJECTED; EGGS UPRIGHT* | NO | 79% | 94 |

[1] Eggs were turned upside down and then righted before injection to mimic mechanical handling of eggs injected upside down. All eggs were sealed after injection with silicone sealant (G.E. TM Silicon II).

A similar injection protocol was used on Day 5 of incubation (data not shown), and resulted in increased hatchability over injection at Day 0.

These results indicate that injection into the albumin via the small end of the egg during early embryonic development can cause an air bubble which interferes with embryonic development. While not wishing to be held to any single theory, the inventors hypothesize that an air bubble resting between the blastodisc and inner shell membrane (floor of the aircell) interferes with formation of the chorioallantoic vasculature system and early respiration of the embryo. By Day 5 of incubation, the chorioallantoic vascular system has already begun to fuse to the innershell membrane, and the effects of the air bubbles would not be as severe.

EXAMPLE 2

Sealing Eggs Prior to Injection Using a Septum

The use of a rubber septum attached to the eggshell, through which the injection would occur, was investigated to determine if this would prevent the entrance of an air bubble during injection. Approximately 100 eggs were examined. A small rubber gas chromatography septum (Fisher Scientific) approximately 5 millimeters in diameter, was attached to the small end of each egg with adhesive. Each egg was injected through the septum at Day 0, while the egg was held upright. Eggs were illuminated and observed on Day 11, and no abnormal development (e.g., frothy albumin, absent air cell, or moving air cell) was observed.

These results indicate that injection of early embryonic eggs through a rubber septum prevented the entrance of an air bubble during injection.

EXAMPLE 3

Comparison of Sealing Prior to and After Injection

A pilot study to compare the use of sealant prior to and after injection was carried out. It was hypothesized that hatchability of eggs sealed and then injected might be improved over eggs injected and then sealed. It was hypothesized that sealant, when applied prior to injection, would cleanse the needle during entry into the egg and forestall entry of outside contaminants as well as prevent the entry of air during injection.

Three treatment groups of 60 eggs each were used: non-injected control eggs; eggs injected (small end) while upright and then sealed (injected-sealed group); eggs sealed and then injected (small end) while upright (sealed-injected group). All eggs were sanitized by dipping into a solution of 5% $H_2O_2$ prior to injection. All eggs were injected on day 0 of incubation with a 20 gauge needle inserted into the small end of the egg while the egg was held in an upright (large end up) position, and eggs were then incubated to hatch in a routine manner. No vehicle was injected into the eggs.

Silicone sealant (G.E. TM Silicone II) was used as the sealant. For sealed-injected eggs, a small amount of sealant (approximately the size of a small pea) was placed on the egg shell at the site of injection, allowed to dry, and the needle inserted through the sealant. The amount of sealant used was such that the needle was inserted through a sealant layer between about 1 millimeter and 3 millimeters thick, and which surrounded the needle. For injected-sealed eggs, the injection was performed and, after the needle was withdrawn, sealant was placed over the injection site.

As seen in Table 2, hatchability of injected-sealed eggs was 86% of non-injected controls, while the hatchability of sealed-injected eggs was actually greater than (105% of) the non-injected controls. These results suggest that injecting eggs upright through a sealant improves hatchability over eggs injected upright and then sealed.

TABLE 2

Day 0 Injection: Hatachability of Eggs Injected Upright

| Treatment | Hatchability (Percent of Noninjected Controls) |
|---|---|
| Noninjected n = 60 | 100 |
| Injected-sealed n = 60 | 86 |
| Sealed-injected n = 60 | 105 |

EXAMPLE 4

Effect of Needle Size and Volume Injected

To determine whether needle size adversely affected hatchability after Day 0 injection, punches of 16 gauge, 18 gauge, 20 gauge and 22 gauge were used. No material was injected into the eggs. The eggs utilized in this experiment were from an older breeder flock exhibiting highly variable percentages of infertiles and early embryonic mortality. However, the results shown in Table 3 indicate a trend for decreased hatchability with increased needle or punch size.

TABLE 3

Day 0 Injection: Effects of Needle Size on Hatchability[1]

| Treatment | Hatchability % | Early Deads | Middle Deads | Late Deads | Live Pips |
|---|---|---|---|---|---|
| Noninjected | 75 | 11 | 0 | 3 | 4 |
| Noninjected + Sealant | 81 | 5 | 0 | 3 | 3 |
| 22 Gauge Punch | 72 | 11 | 1 | 2 | 4 |
| 20 Gauge Punch | 67 | 12 | 2 | 3 | 4 |
| 18 Gauge Punch | 60 | 15 | 2 | 3 | 6 |
| 16 Gauge Punch | 66 | 11 | 2 | 4 | 6 |

[1] Hatchability is based on chicks which hatched from all eggs set and includes infertiles, malpositions and malformations.

EXAMPLE 5

Decontamination of Needle by Sealant

Experiments were performed to test whether insertion of the injection needle through the sealant contributed to needle sanitation, thereby reducing egg-to-egg bacterial contamination when a needle was used for multiple injections. A needle was dipped in a broth culture of *Escherichia coli* and then either inserted into a vial containing 1 ml of sterile water or into a vial containing 1 ml of sterile water which had been covered by a plug of silicone gel (G.E. ™ Silicone II) similar in amount to that used on eggs prior to injection (see Example 3). To determine if antibiotic in the sealant would improve needle sanitation, in an additional treatment the needle was inserted through silicone sealant (G.E. ™ Silicone II) into which GARASOL ™ (Schering Corp., Kenilworth, N.J.) had been mixed at a concentration of 1 mg/gram (0.0625 ml GARASOL ™ /6.25 grams of silicone). Results are presented in Table 4.

TABLE 4

Injection through Silicone and Decontamination of *E. Coli* Contaminated Needles

| Untreated Needle Contamination Mean[1] CFU/needle | Needle Inserted Through Silicone Mean CFU/needle | Needle Inserted Through Silicone Containing GARASOL ™ Mean CFU/needle |
|---|---|---|
| 90,000,000 | <1000 | 4,900,00 |
| 86,000,000 | <1000 | 12,800,00 |
| 89,000,000 | 8,100,000 | 4,300,000 |

[1]Each mean represents serial dilutions of one needle tested. The minimum detection limit for this experiment was 1000 Colony Forming Unit (CFU).

The data in Table 4 suggest that inserting a needle through silicone sealant during egg injection significantly reduces contamination (~3 logs) of the needle even in the face of a high bacterial challenge. Interestingly, although the silicone sealant mixed with GARASOL ™ (Schering Corp., Kenilworth, N.J.) reduced the bacterial load on the needle, it only reduced it by one log. Possibly the addition of antibiotic altered the consistency of the silicone, rendering it less effective in its sanitizing properties.

EXAMPLE 6

Delivery of Compounds at Day 0

As not all compounds designed for injection will be soluble in water or PBS, experiments were designed to indicate possible problems regarding early egg injection techniques using various excipients. These experiments were not intended to clearly discern small differences in hatchability. Treatment groups consisted of 120 eggs per group (two trials of 60 eggs per trial). Isopropanol was chosen as a diluent because many lipophilic or hydrophobic compounds which are insoluble in water can initially be solubilized in isopropanol and then diluted in water. Silica was incorporated into the experimental design as a representative polymer (inclusion of polymers in excipients allows proteins to adhere to the polymer resulting in a slow release formulation as well as increasing the antigenicity of antigens). Also tested as an excipient was MOLECUSOL ™ (Pharmatec, Inc.) which is a beta-cyclodextran.

Hatchability was evaluated following injection of 50 μl of each excipient tested (Table 5). Day 0 broiler eggs were injected in the small end while held upright; sealant was applied to the injection site prior to injection (see Example 3). None of the excipients tested significantly depressed hatchability.

TABLE 5

Day 0 Injection: Hatchability Following Administration of Vehicles

| Treatment Group | hatchability (means[1]) | early deads | middle deads | late deads |
|---|---|---|---|---|
| Noninjected control | 79.7 | 7.4 | 1.65 | 0.8 |
| Silica in 5% Isopropanol | 78.7 | 8.1 | 1.1 | 0 |
| Silica in 20% isopropanol | 82.1 | 5.9 | 1 | 1.9 |
| Molecusol 1% | 84.8 | 9.9 | 1.5 | 0 |
| Molecusol 5% | 82.5 | 9.2 | 1 | 3.0 |
| isopropanol 5% | 81.8 | 7.3 | 0 | 3.2 |
| isopropanol 20% | 75.1 | 9.3 | 1.5 | 0 |

[1]Means are based on two trials each consisting of 60 eggs per treatment group (n = 120).

The results set forth in Table 5 indicate that multiple vehicles are suitable for use in the injection technique described above.

A further experiment using the quinolone antibiotic Sarafloxacin (Abbott Laboratories) was performed. Sarafloxacin is administered subcutaneously to day old chicks at 0.1 mg for control of bacterially related early mortality. A stock sarafloxacin solution, 50 mg/ml, (provided by Abbott Laboratories) was diluted in sterile water to concentrations of 5.0, 1.0, 0.5 and 0.1 mg/ml. Injection of 50 μl delivered 0.25, 0.05, 0.025 and 0.005 mg/egg, respectively. The doses injected at Day 0 were 2.5×, 0.5×, 0.25× and 0.05× the dose given to chicks at hatch. Injection was performed on Day 0 of incubation through silicone sealant (G.E. ™ Silicone II) applied to the small end of eggs; eggs were held upright during injection (see Example 3).

TABLE 6

Day 0 Injection: Hatchability Following Sarafloxacin Administration

| Treatment Group | Hatchability (means %)[1] | Early Deads | Middle Deads | Late Deads |
|---|---|---|---|---|
| Noninjected Control | 88.0 | 3.4 | .80 | 1.6 |
| Vehicle | 89.7 | 6.75 | .85 | 0 |
| 0.25 mg/egg (2.5 ×) | 84.7 | 5.8 | .80 | 1.6 |
| 0.05 mg/egg (0.5 ×) | 86.6 | 4.9 | .80 | 0 |
| 0.025 mg/egg (0.25 ×) | 78.5 | 5.0 | 1.65 | 3.35 |
| 0.05 mg/egg (0.05 ×) | 82.7 | 5.95 | .85 | 1.7 |

[1]Percents based on normal hatched chicks divided by total eggs set; Means are based on two hatchability trials each consisting of 60 eggs per treatment group (n = 120).

Although all doses of Sarafloxacin administered resulted in a slight depression in hatchability, the effects were inconsistent across trials and the means do not demonstrate dose dependent effects since some lower doses depressed hatchability more than the maximum dose administered. These results indicate that the injection technique described above is capable of delivering an active agent without significantly depressing hatchability.

EXAMPLE 7

Combined Sanitation and Injection at Day 0

A technique combining sanitation of the egg shell injection site with injection through a sealant was tested to determine effects on hatchability as compared to non-injected controls. The small end of each egg to be injected was dipped in either a 5% $H_2O_2$/quaternary ammonium sanitizer, or a chlorine based sanitizer consisting of 0.5% CHLOROX ™, for 4 minutes. A small dab (approximately the size of a small pea) of silicone sealant (G.E. ™ Silicone II) was then applied to the injection site on the small end, and then 50 μl of saline was injected through the sealant into the egg albumin using a 22 gauge needle, with the egg held upright. The data from two trials is presented in Table 7. Each treatment group used 300 eggs (two trials of 150 eggs).

TABLE 7

| Group | Injected | Sanitized | Hatch % | Bacteria Contaminated Eggs % | Mold Contaminated Eggs % | Bacteria Contaminated Yolk Sacs % |
|---|---|---|---|---|---|---|
| 1 | No | No | 79 | 4.7 | 1.3 | 4.6 |
| 2 | No | Yes | 76 | 1.4 | 0.7 | 0.5 |
| 3 | Yes | No | 78 | 4.0 | 1.3 | 8.5 |
| 4 | Yes | Yes | 77 | 5.3 | 0 | 2.0 |

The data set forth in Table 7 show that injected eggs have hatchability rates equivalent to noninjected controls. While sanitation of injected eggs does not appear to decrease the rate of bacterially contaminated eggs over non-sanitized injected eggs, the rate of mold contamination and bacterially contaminated yolk sacs of hatched chicks appeared to be reduced in sanitized injected eggs over non-sanitized injected eggs.

The foregoing is illustrative of the present invention and is not to be construed as limiting thereof. The invention is defined by the following claims, with equivalents of the claims to be included therein.

That which is claimed is:

1. A method of introducing a substance into a bird egg through the shell thereof, comprising the steps of:
    applying a seal to the exterior of the shell;
    inserting an injection device through said seal and into the egg;
    injecting said substance through said injection device and into the interior of the egg; and
    withdrawing said injection device from the egg through said seal;
    whereby said substance is deposited in the interior of the egg.

2. A method as in claim 1 wherein said seal is applied to the small end of the egg.

3. A method as in claim 1 wherein said egg is oriented with the small end down and said injection device travels upwardly through the egg shell at the small end thereof and into the interior of the egg.

4. A method as in claim 1 wherein said substance injected is a liquid.

5. A method as in claim 1 wherein said substance injected is a solid.

6. A method as in claim 1 wherein said withdrawing step is followed by the step of incubating said egg to hatch.

7. A method as in claim 1 wherein the egg is selected from the group consisting of turkey eggs, chicken eggs, quail eggs, duck eggs, goose eggs, ostrich eggs and pheasant eggs.

8. A method as in claim 1 wherein said egg is injected during the first quarter of incubation.

9. A method as in claim 1 wherein said egg is injected prior to the first day of incubation.

10. A method as in claim 1, wherein said applying step comprises the steps of:
    depositing a liquid sealant material on the egg; and then
    curing said liquid sealant on the egg to form an elastic seal thereon.

11. A method as in claim 1, wherein said applying step comprises the steps of:
    providing a preformed elastic seal member; and then
    adhering said preformed elastic seal member to said egg.

12. A method as in claim 1, wherein said substance is deposited in the interior of the egg in the region defined by the amnion, the albumin or the yolk sac.

13. A method of introducing a substance into a bird egg through the shell thereof, comprising:
    applying a seal to the exterior of the shell;
    inserting an injection device through said seal and into the egg, which egg is in the first quarter of incubation thereof;
    injecting said substance through said injection device and into the region of the egg defined by the albumin;
    withdrawing said injection device from the egg through said seal; and then
    incubating said egg to hatch.

14. A method as in claim 13 wherein said seal is applied to the small end of said egg.

15. A method as in claim 13 wherein said egg is oriented with the small end down and said injection device travels upwardly through the egg shell at the small end thereof and into the interior of the egg.

16. A method as in claim 13 wherein said material injected into said egg is a liquid.

17. A method as in claim 13 wherein said material injected into said egg is a solid.

18. A method as in claim 13 wherein said egg is selected from the group consisting of turkey eggs, chicken eggs, quail eggs, duck eggs, goose eggs, ostrich eggs and pheasant eggs.

19. A method as in claim 13 wherein said egg is injected prior to the first day of incubation.

20. A method as in claim 13, wherein said applying step comprises the steps of:
    depositing a liquid sealant material on the egg; and then
    curing said liquid sealant on the egg to form an elastic seal thereon.

21. A method as in claim 13, wherein said applying step comprises the steps of:
    providing a preformed elastic seal member; and then
    adhering said preformed elastic seal member to said egg.

22. A method as in claim 13, wherein said seal contains an antibacterial agent.

* * * * *

UNITED STATES PATENT AND TRADEMARK OFFICE
CERTIFICATE OF CORRECTION

PATENT NO. : 5,339,766

DATED : 23 August 1994

INVENTOR(S) : Patricia V. Phelps, Julius K. Tyczkowski, Toni O. O'Connell, Ann B. Gore It is certified that error appears in the above-indentified patent and that said Letters Patent is hereby corrected as shown below:

In the drawings, Sheet 1, Figures 1-3, should appear as per the attached sheet of drawings.

Signed and Sealed this

Twenty-second Day of November, 1994

Attest:

BRUCE LEHMAN

*Attesting Officer*    *Commissioner of Patents and Trademarks*